(12) United States Patent
Peschl (10) Patent No.: US 12,330,130 B2
(45) Date of Patent: Jun. 17, 2025

(54) LED LAMP MODULE AND DEVICE FOR CARRYING OUT A PHOTOCHEMICAL REACTION

(71) Applicant: Peschl Ultraviolet GmbH, Mainz (DE)

(72) Inventor: Alexander Peschl, Mainz (DE)

(73) Assignee: Peschl Ultraviolet GmbH, Mainz (DE)

( * ) Notice: Subject to any disclaimer, the term of this patent is extended or adjusted under 35 U.S.C. 154(b) by 0 days.

(21) Appl. No.: 18/848,982

(22) PCT Filed: Apr. 11, 2023

(86) PCT No.: PCT/EP2023/059385
§ 371 (c)(1),
(2) Date: Sep. 20, 2024

(87) PCT Pub. No.: WO2023/194621
PCT Pub. Date: Oct. 12, 2023

(65) Prior Publication Data
US 2025/0161903 A1 May 22, 2025

(30) Foreign Application Priority Data

Apr. 7, 2022 (WO) .................. PCT/EP2022/059279

(51) Int. Cl.
*B01J 19/12* (2006.01)
*B01J 19/00* (2006.01)
(Continued)

(52) U.S. Cl.
CPC .......... *B01J 19/122* (2013.01); *B01J 19/0006* (2013.01); *B01J 19/123* (2013.01);
(Continued)

(58) Field of Classification Search
CPC .... B01J 19/122; B01J 19/123; B01J 19/0006; B01J 2219/0801; B01J 2219/1203;
(Continued)

(56) References Cited

U.S. PATENT DOCUMENTS

2017/0030567 A1 2/2017 Sun et al.
2017/0167712 A1 6/2017 Melzner
(Continued)

FOREIGN PATENT DOCUMENTS

CN 108180403 A 6/2018
DE 202011050253 U1 8/2011
(Continued)

*Primary Examiner* — Lessanework Seifu
(74) *Attorney, Agent, or Firm* — Smartpat PLC (57) ABSTRACT

An LED lamp module for carrying out a photochemical reaction has a carrier body on which a plurality of LEDs are fastened. The carrier body is arranged in an interior space of the LED lamp module, delimited by a transparent wall element and a housing. An electrical supply line for the electrical connection of the LEDs extends through the housing. The LEDs are divided into LED groups and connected in series in each LED group. A driver is assigned to each LED group as constant current source for the operation of the LEDs. Each driver is arranged adjacent to its LED group on the carrier body in the interior space of the LED lamp module, and is connected in series to its LED group, thereby forming an LED current branch. The LED current branches are connected in parallel to a constant voltage source via the supply line.

15 Claims, 5 Drawing Sheets

(51) Int. Cl.
*C02F 1/32* (2023.01)
*C12M 1/00* (2006.01)

(52) U.S. Cl.
CPC .............. *C02F 1/325* (2013.01); *C12M 31/10* (2013.01); *B01J 2219/0801* (2013.01); *B01J 2219/1203* (2013.01); *C02F 2201/3222* (2013.01); *C02F 2201/3225* (2013.01); *C02F 2201/3227* (2013.01); *C02F 2201/326* (2013.01)

(58) Field of Classification Search
CPC ................ C02F 1/325; C02F 2201/326; C02F 2201/3221; C02F 2201/3222; C02F 2201/3225; C02F 2201/3337; C12M 31/10; C12M 31/02
See application file for complete search history.

(56) References Cited

U.S. PATENT DOCUMENTS

| | | |
|---|---|---|
| 2020/0124266 A1 | 4/2020 | Di et al. |
| 2022/0072871 A1 | 3/2022 | Meyer et al. |
| 2022/0204898 A1 | 6/2022 | Peschl et al. |

FOREIGN PATENT DOCUMENTS

| | | |
|---|---|---|
| DE | 202014103329 U1 | 9/2014 |
| DE | 102014012218 A1 | 2/2016 |
| DE | 102014012219 A1 | 2/2016 |
| DE | 102016224064 A1 | 6/2018 |
| EP | 2701473 A2 | 2/2014 |
| KR | 20160100712 A | 8/2016 |
| WO | 2016026576 A1 | 2/2016 |
| WO | 2020148289 A1 | 7/2020 |
| WO | 2020228980 A1 | 11/2020 |

Fig. 1

Prior Art

LED LAMP MODULE AND DEVICE FOR CARRYING OUT A PHOTOCHEMICAL REACTION

CROSS-REFERENCE TO RELATED APPLICATION

This application is a national stage application, filed under 35 U.S.C. § 371, of International Patent Application PCT/EP2023/059385, filed on Apr. 11, 2023, which claims the benefit of international Patent Application PCT/EP2022/059279, filed with the European Patent Office on Apr. 7, 2022.

TECHNICAL FIELD

The present disclosure relates to an LED lamp module, which is formed for the use in a device for carrying out a photochemical reaction on an industrial scale with a large number of LEDs or LED density, respectively, and to a device for carrying out a photochemical reaction, which has at least one such LED lamp module.

BACKGROUND

Low pressure or medium pressure radiators are currently often still used for carrying out photochemical reactions on an industrial scale at which reaction chambers can also traverse several meters because they can have dimensions in a corresponding magnitude. However, the operation thereof is associated with high power consumption and regular monitoring in relatively short time intervals are required with increasing age because the radiation intensity decreases significantly and the radiation spectrum can shift.

Attempts are thus made to also use LED lamps in the photochemical field, which, compared to the conventional low pressure or medium pressure radiators, have a small power consumption, a long service life and a high switching resistance even in the case of spontaneously full luminous flux. In the present case, all processes induced by means of photons, e.g., photochemical or photocatalyzed syntheses, so-called AOPs ("advanced oxidation processes") and UV disinfection of water and surfaces, are considered to be photochemical reactions.

If LEDs are to be used in photoreactors for chemical syntheses, e.g., photochlorination or photobromination as immersion lamp, the used lamp module does not only need to meet the increased demands with respect to the surrounding reaction conditions, which can deviate very significantly from the ambient pressure and room temperature but also has to have dimensions adapted to the size of the reaction chamber. The use of LEDs as lamp module on an industrial scale is thereby delimited by the number and density of the LEDs, which, due to their mode of operation, is possible with low voltage and the high current, which is required for a high radiation power. If the LEDs are operated with high currents for a high light yield or radiation intensity, respectively, an effective heat dissipation from the LEDs is required in order to avoid locally high temperatures in order to maintain the service life thereof. For the effective heat dissipation, the LEDs are arranged on a mostly metallic carrier body, which can have structures for the heat dissipation, such as, for example, cooling channels, through which a cooling fluid is guided. A direct cooling of LEDs by means of electrically non-conductive cooling liquid is also known. However, the operation of the LEDs at the power maximum for carrying out photochemical reactions is disadvantageous for the service life of the LEDs even in the case of effective heat dissipation.

An LED lamp module for carrying out photochemical reactions with a significantly increased number of LEDs is known from DE 10 2014 012 219 B4 for the adaptation of the dimensions for the use on an industrial scale. The carrier body for the LEDs thereby has a cooling path, which is connected to a cooling circuit via a head part of the lamp module. To improve the power supply, the carrier body is further formed with at least one longitudinally axial or axially parallel chamber, through which a line for the power supply/control extends from the head part all the way to a contact element of the LEDs. The power supply and control device, which can comprise, for example, ballast or power electronics, respectively, driver and power supply units, is thereby an external power supply and control device, which is arranged outside of the photoreactor and which is connected via an electrical connecting device of the head part. Alternatively, the power supply and control device can be accommodated in the head part, so that the temperature-sensitive power electronics or the LED drivers, respectively, can be cooled through sections of the cooling circuit provided for the LEDs.

For the use as immersion lamp in a device for carrying out photochemical reactions, an LED lamp module is usually arranged in a transparent cladding tube, which is closed on one side for the most part. The head part, via which the electrical supply of the LED lamp module takes place, can close the open end of the cladding tube. The carrier body can have a hexagonal or octagonal cross section and can thus provide six or eight side surfaces, to which LEDs can be fastened. For this purpose, the LEDs are usually arranged in a predetermined number on printed circuit boards, which have corresponding conductor tracks for the connection of the LEDs. The printed circuit boards arranged on a side surface of the carrier body in each case form an LED strand, which is operated by means of a driver. In the case of a strand voltage of 300 V and a forward voltage of the LEDs of 4 V, for example, the maximum number of the LEDs per strand is 75 pieces, which can be operated by means of a driver. With a currently maximum overall length of the printed circuit boards of approx. 50 cm, which are each fitted with 18 or 15 LEDs, 4 or 5 printed circuit boards, connected in series, form one strand, so that a maximum length of the lamp module of 200 to 250 cm results. If an LED strand with a maximum LED number is in each case provided on each side surface of the hexagonal or octagonal carrier body, the LED lamp has 450 or 600 LEDs.

Depending on the process and desired homogeneity, the density of 0.375 to 0.3 LED/cm, which can be attained with the number of 75 LED per strand at a length of 200 to 250 cm, can be significantly too low. However, a higher density, i.e., a larger number of LEDs per cm of lighting length, can only be attained by shortening the LED lamp module due to the limitation by 300 V of ballast voltage per strand, which contradicts the desired lengthening of the lamp module for the adaptation to the dimensions of the reaction chambers on an industrial scale. In addition, two connecting contacts are required for each ballast or driver, respectively, which are introduced into the head part of the lamp, e.g., via plugs. If an LED strand is in each case provided on each side surface of a hexagonal or octagonal carrier body, six or eight ballasts/drivers are accordingly required, which then necessitate 12 or 16 connecting contacts. With a given diameter of the lamp or of the head part, respectively, the available space for connections is limited. The number of the ballasts or drivers, respectively, which can be connected to an LED lamp for the operation of a respective LED strand, is thus also limited.

An upscaling of LED lamps, which are to have a significantly larger number of LEDs, in order to provide for a high LED density, which is required for carrying out a photochemical reaction, in particular also in the case of a lamp length of over 200 to 250 cm, is thus not readily possible because a correspondingly large number of ballasts/drivers, each with two connecting contacts, would be required for the very large LED number and the space for connections on the head part of the lamp is limited.

SUMMARY

The present disclosure is based on the object of providing a scalable LED lamp module formed for photochemical reactions on an industrial scale with an improved LED density.

This object is solved by an LED lamp module as disclosed and claimed.

A further object of providing a device with an improved LED lamp module for carrying out a photochemical reaction is solved by the device as disclosed and claimed.

According to a first embodiment, the LED lamp module, which is formed for the arrangement in a device for carrying out a photochemical reaction, has a plurality of LEDs and a shaping carrier body. The LEDs are fastened to the carrier body, which is arranged with the LEDs in an interior space of the LED lamp module, which is delimited by a transparent wall element and by a housing element. The transparent wall element is arranged in a corresponding manner to the LEDs and at least one electrical supply line for the electrical connection of the LEDs extends through the housing element. The plurality of LEDs is thereby divided into LED groups, which have a predetermined number of LEDs, wherein the LEDs of each LED group are connected in series, and each LED group is in each case assigned to a driver device as constant current source for the operation of the LEDs of the respective LED group and is connected thereto. Each driver device is arranged adjacent to the LED group assigned to it on the carrier body in the interior space of the LED lamp module, wherein each driver device is connected in series to the respective assigned LED group and forms an LED current branch. The LED current branches formed by means of the driver devices with the LED groups are thereby connected in parallel, wherein the LED current branches connected in parallel are connected to a constant voltage source via the supply line. The constant voltage of the constant voltage source is converted into constant current by the driver device of each LED group.

By means of the circuit for the supply of the LEDs, which is mixed, which contains elements of series connection as well as of parallel connections, the LED lamp module can be scaled easily by multiplying the parallel LED current branches and the number of the LEDs can thus be increased significantly without the number of the supply lines required for this purpose with the electrical connections on the housing element increasing because the voltage of the parallel LED current branches is constant.

Forward and return conductors of the LED circuit with the LED current branches connected in parallel are combined herein with the term of the supply line. An LED lamp module can thereby have more than one LED circuit with a respective supply line as above. A connecting device, which accordingly has two connecting contacts for forward and return conductors of the supply line, is provided on the housing element for each supply line. The supply line with forward and return conductor can be connected in one cable via a connecting plug, which has the two connecting contacts. It can also be provided, however, that separate cables are provided, which each have a connecting plug with one of the connecting contacts, for forward and return line of a supply line.

Due to this mixed circuit with the integrated driver devices, an LED lamp module can advantageously not only be embodied in a desired length, even of more than 200 cm, but can also be variably adapted to the requirements of the respective photochemical reaction with respect to LED density, power density and LED forward voltage. This is so because the power density required for carrying out a photochemical reaction can vary strongly. For example, LED lamp modules with a high LED density and low power are suitable for carrying out a photochlorination reaction, while carrying out a photoredox reaction requires LED lamp modules, which have a high LED density with high power. Due to this mixed circuit with the integrated driver devices, an LED lamp module can be embodied with an LED density of at least 125 LEDs/m and/or a power density of at least 35 W/m and/or an LED forward voltage of at least 3 V per LED in the designed length, even of more than 200 cm.

Further embodiments of the LED lamp module provide that the predetermined number of LEDs of all LED groups is identical and is maximally 25. With an exemplary forward voltage of each LED of 4 V, the constant voltage of the constant voltage source then lies at maximally 100 V. It is preferably possible that the predetermined number of LEDs is maximally 20, so that the constant voltage of the constant voltage source with the exemplary forward voltage of each LED of 4 V is maximally 80 V. In particular, the predetermined number of LEDs is maximally 15, so that the constant voltage of the constant voltage source with the exemplary forward voltage of each LED of 4. Vis maximally 60 V. Due to the LED groups, which are connected in parallel, with an assigned driver device, the constant voltage can be reduced significantly compared to the prior art. Embodiments with an advantageously low voltage of maximally 60 V DC can be preferred because ATEX plug connectors with a suitable dimensioning can then be used for the connection of the supply line to the housing element, so that the LED lamp module can be used in potentially explosive regions, if, e.g., reactants or products of the photochemical reaction with air can form an explosive atmosphere.

According to a further embodiment of the LED lamp module, the LED current branches from the LED groups with the driver devices assigned to them can be formed as integrated circuit components on printed circuit boards, which are fastened to the carrier body, wherein one or several of the LED groups with the respective driver device is/are arranged on each printed circuit board. A modular system, by means of which an LED lamp can be designed and expanded flexibly, is created in this way by means of the printed circuit boards. There are no limitations with respect to the length of the lamp module or the number of the LED current branches or of the printed circuit boards, respectively.

An LED lamp module can further be further developed to the effect that at least one control and/or regulating element and at least one measuring device is assigned to each LED group, which is selected from a group, which can include a current measuring device, a voltage measuring device, a temperature measuring device and a photon measuring device. Alternatives to the at least one measuring device or additionally thereto, at least one switch element can further be assigned to each LED group. The control and/or regulating element is thereby communicatively connected to the at least one measuring device and is formed to control the switch element as a function of a measuring value captured by the at least one measuring device, in order to activate or deactivate and/or to dim the LEDs of the assigned LED group as a function of the measuring values. It goes without saying that the control and/or regulating element is also communicatively connected to the at least one switch element for this purpose. The control and/or regulating element can further be formed to control the driver device of the assigned LED group for regulating the constant current, in order to operate the LEDs of the assigned LED group with a predetermined power.

A correct operation can be ensured by means of the integration of a current and voltage measurement for each LED group on the printed circuit board. In case of a fault, e.g., failure of an LED in an LED group, which is detected by means of the integrated current and voltage measurement, the assigned LED group can be deactivated and it can thus be avoided that the remaining LEDs of the group are overloaded. Due to the failure of an LED, a hotspot is created, which can lead to the failure of further LEDs and thus to further hotspots, which can be reliably avoided in an explosive atmosphere, in which the LED lamp module can be located, by means of the deactivation, so that the explosion protection is improved. A hotspot can also be determined by means of the integrated temperature measurement, but which mainly serves the purpose that the LEDs, the optical output of which is not only a function of current but also of temperature, supply the desired radiation power. An operation of the LEDs within a predetermined temperature window can thus be ensured by means of the temperature measurement, so that it is prevented that the LEDs become too warm. The optional photon measurement can also be used to adjust the optical output of the LED groups.

According to a further embodiment, the measuring device and/or the switch element such as the driver device can be arranged as integrated circuit components on the printed circuit board of the assigned LED group.

According to a further embodiment of an LED lamp module, the control and/or regulating element can likewise be formed as integrated circuit component on the printed circuit board of the assigned LED group. Alternatively, each control and/or regulating element assigned to an LED group can be arranged outside of the interior space. In both cases, the control and/or regulating elements of all LED groups are communicatively connected to one another and/or to a higher-ranking control and/or regulating unit and are formed to adapt the predetermined radiation power of the LEDs of each LED group to one another, in order to attain a homogenous total radiation power. Alternatively, individual LED groups can be activated and deactivated, in order to use only portions of the LED lamp module for the radiation emission. The control and/or regulating units, which are connected to one another and/or to a higher-ranking control and/or regulating, can further be formed to assign a unique ID to each LED group and/or to collect operating data and/or operating time of each LED group.

A further embodiment of the LED lamp module can provide that the LED lamp module has at least one supply rail for receiving the at least one supply line within the interior space.

According to a preferred embodiment of the LED lamp module, the carrier body is a carrying cage with a grid structure, of the carrying structures, to which the LED groups are fastened, and at least one support structure for the positioned arrangement of the LED groups fastened to the carrying cage within the interior space.

According to an advantageous embodiment, the at least one supply rail can be provided by at least one rail structure of the carrying cage, so that the LEDs do not shade due to the supply line(s).

According to a further embodiment, an LED lamp module can further have a cooling circuit with an electrically non-conductive liquid, wherein the housing element has an inlet connection and a discharge connection for the connection of the interior space to the cooling circuit, so that the interior space is completely filled with the electrically non-conductive liquid. The driver devices and the LEDs as well as optionally the further circuit components can thus be cooled jointly by means of the electrically non-conductive liquid. This cooling is particularly effective when the carrier body is embodied as carrying cage.

According to a specific embodiment, the LED lamp module is formed as immersion lamp with a longitudinal axis, wherein the transparent wall element is a transparent cladding tube, which is closed on one side and which is arranged coaxially around the carrier body with the LEDs. The housing element has a head part, which is arranged on an open end of the cladding tube.

In a further development of this, the carrier body formed as carrying cage has, on at least one longitudinally axial end, the at least one support structure for the positioned arrangement within the interior space, wherein the support structure is formed for the centered arrangement on the head part and/or the closed end of the cladding tube. Alternatively or additionally, the head part has passage openings, wherein the inlet connection and the discharge connection in each case extend through one of the passage openings or are connected thereto. On the side of the interior space, the inlet connection is thereby preferably connected to a tube structure, which is arranged in the carrier body formed as carrying case and which extends longitudinally through the carrying cage as coolant inlet section, which provides an inlet opening on an end of the interior space spaced apart from the head part. On an end of the interior space close to the head part, a discharge opening is provided by means of the discharge connection, which extends through the head part, or by means of the passage opening, which is connected to the discharge connection.

Alternatively to an immersion lamp, an LED lamp module can, according to a further embodiment, be formed as surface radiator, wherein the transparent wall element is a transparent flat window pane, and the housing element is a housing, which has a base and side walls. The window pane closes an open surface, which is delimited by side walls, wherein the LEDs arranged on the carrier body are arranged between the window pane and the base in a plane parallel to the window pane.

According to a further development of the device, the carrier body formed as carrying cage is arranged with the at least one support structure on the base of the housing, wherein the carrying structures, to which the LEDs are fastened, are formed on a side of the carrying cage facing away from the at least one support structure. A dimension of the carrying cage between the carrying structures and the at least one support structure thereby determines a distance of the LEDs from the window pane. Alternatively or additionally, the housing has, on opposite sides of the interior space, at least one inlet opening, which is connected to the inlet connection, and at least one discharge opening, which is connected to the discharge connection.

According to a first embodiment, a device for carrying out a photochemical reaction has a photoreactor, on or in which at least one lamp module is arranged, which emits radiation with a wavelength, which is suitable for the photochemical reaction, wherein the lamp module is an LED lamp module as described.

Further embodiments as well as some of the advantages, which are associated with these and further embodiments, become clear and better understandable by means of the following detailed description with reference to the accompanying figures. Objects or parts thereof, which are essentially identical or similar, can be provided with the same reference numerals. The figures are only a schematic illustration of an embodiment of the invention.

DETAILED DESCRIPTION

The present disclosure relates to an LED lamp module, which is formed for use in a device for carrying out a photochemical reaction with an LED density, power density and LED forward voltage adapted for this purpose in a desired length, which can even be more than 200 cm.

The LED lamp module can have an LED density of at least 125 LEDs/m and/or a power density of at least 35 W/m and/or a forward voltage of at least 3 V per LED.

The present disclosure further also relates to a device for carrying out a photochemical reaction, which has such an LED lamp module.

Figure 1:
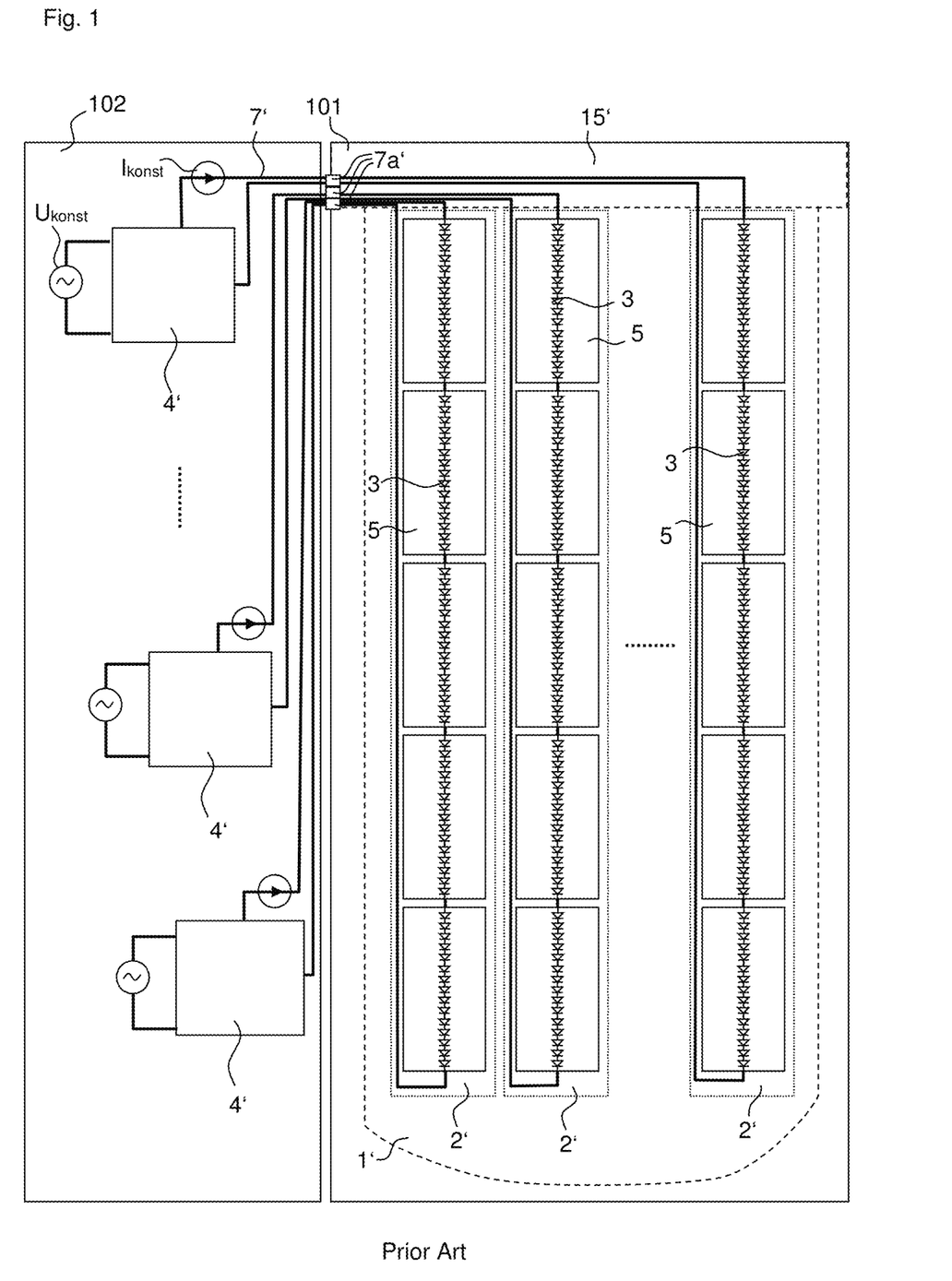
FIG. 1 shows a schematic illustration of a device for carrying out a photochemical reaction with an LED lamp module from the prior art.

In the prior art, an LED lamp module 1' is used for carrying out a photochemical reaction, which, as illustrated schematically in FIG. 1, can be used as an immersion lamp in a photoreactor 101, in order to expose a medium presented therein to an electromagnetic radiation, which causes the desired photochemical reaction. For a conversion on an industrial scale, it is required that photoreactors have dimensions of several meters, which require correspondingly dimensioned lamps, in order to attain an even radiation of the reactor volume. In contrast to conventional low pressure or medium pressure radiators, which are available with corresponding dimensions, the length of the LED lamp modules 1' of the prior art is limited in the case of an LED density specified for a minimum power.

An LED strand 2' can maximally have 75 LEDs 3 connected in series, which are operated with a strand voltage of maximally 300 V by a driver 4', which provides a constant current $I_{const}$. If these 75 LEDs are distributed to four or five printed circuit boards 5 with a maximum printed circuit board length of 50 cm, the LED lamp module 1' or the LED strand 2', respectively, can in fact reach a lighting length of 200 or 250 cm. However, this is associated with an LED density of 37.5 LEDs/m or 30 LEDs/m, respectively, which can be significantly too low, depending on the process and desired homogeneity. Even though a higher LED density would be possible with shorter LED lamp modules 1', it would be disadvantageously associated with an uneven illumination of a correspondingly large-volume photoreactor 101.

A further limitation of the LED lamp module 1' from the prior art lies in that a driver 4' is to be provided in each case for each LED strand 2'. An LED lamp module 1' with six or eight LED strands 2' accordingly requires six or eight drivers 4', which are usually accommodated in a separate control cabinet 102 spaced apart from the photoreactor 101, in order to be connected to a voltage source $U_{const}$. And due to the fact that the LED lamp module 1' has to further have a connecting device 7a' with two connecting contacts each for forward and return conductors of the supply line 7' on the head part 15' for each LED strand 2' for the connection to the assigned driver 4' via a supply line 7', the number of the LED strands 2' is limited by the space available on the LED lamp module 1' for connecting contacts.

The LED lamp module 1, for which different examples are shown in FIGS. 2 to 7, overcomes the limitation of the prior art: for the use in devices 100 for carrying out photochemical reactions, the LED lamp module 1 has an LED density, which is independent of the lamp length, of at least 125 LEDs/m and/or a power density of at least 35 W/m and/or a forward voltage of at least 3 V per LED.

Figure 2:
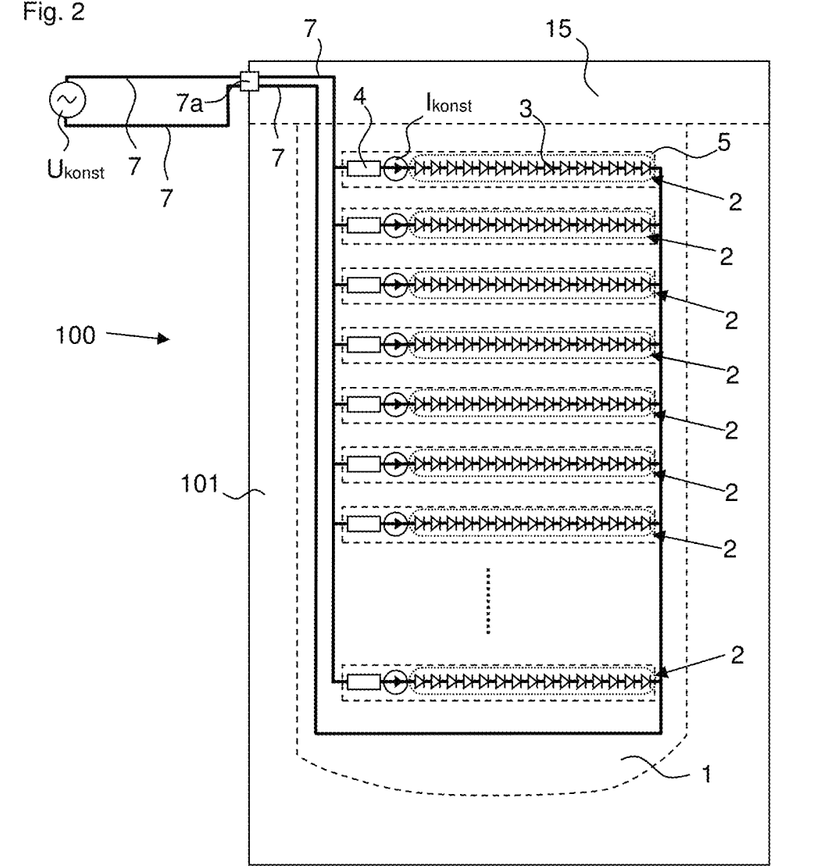
FIG. 2 shows a schematic illustration of a device for carrying out a photochemical reaction with an LED lamp module.
Figure 8:
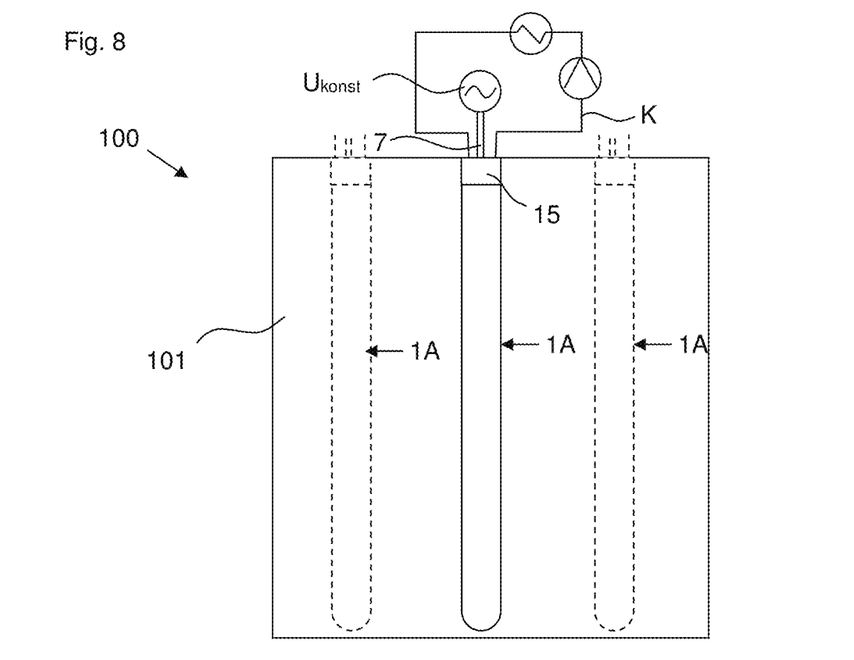
FIG. 8 shows a schematic illustration of a device for carrying out a photochemical reaction with an LED lamp module in the embodiment as immersion lamp.
Figure 9:
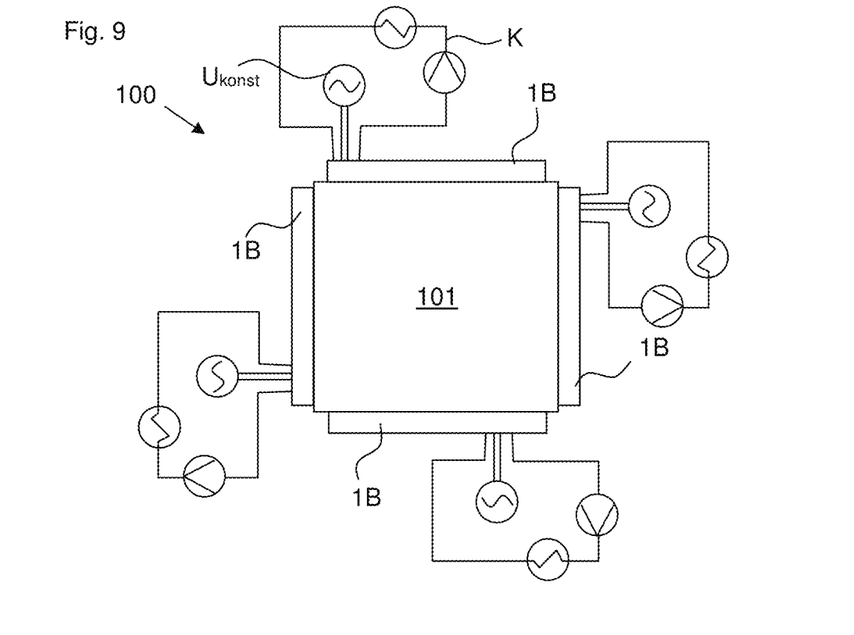
FIG. 9 shows a schematic illustration of a device for carrying out a photochemical reaction with an LED lamp module in the embodiment as surface radiator.

The use of an LED lamp module 1 in a device 100 for carrying out a photochemical reaction is illustrated schematically in FIG. 2, FIGS. 8 and 9 show further examples of devices 100 for carrying out a photochemical reaction with LED lamp modules 1, which are embodied differently. In each LED lamp module 1, a plurality of LEDs 3 is fastened to a carrier body 6, the shape of which is adapted to the geometry of the LED lamp module 1 and which provides at least one surface for fastening the LEDs 3. By means of the orientation of the fastening surface, a radiation direction of the LEDs 3 is specified, with which the radiation characteristic of the LED lamp module 1 is defined. The radiation characteristic can be modified thereby with the use of reflection, refraction and/or filter elements.

Figure 3:
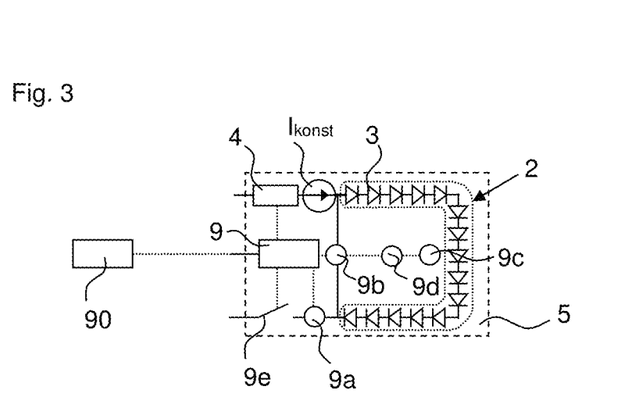
FIG. 3 shows a schematic illustration of an LED group of an LED lamp module.
Figure 4:
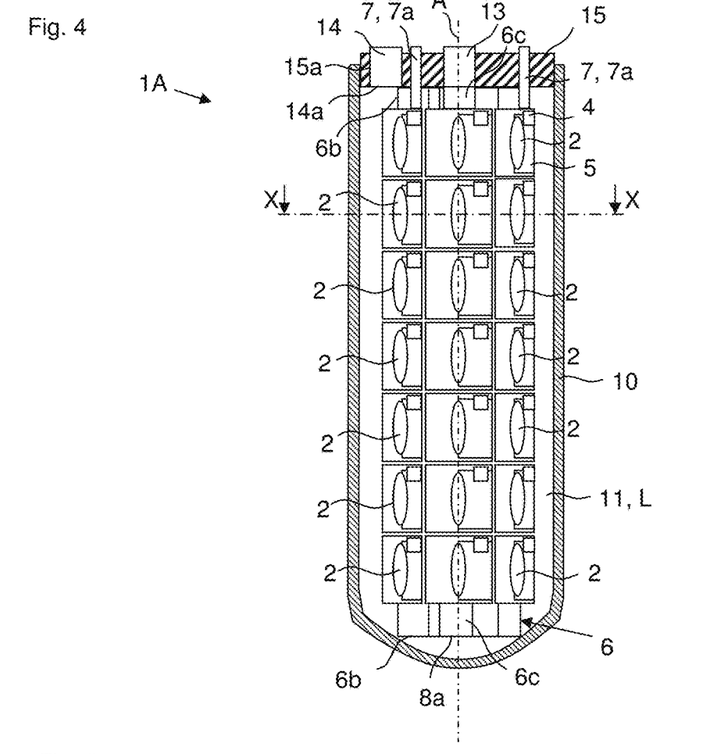
FIG. 4 shows a partially cut side view of an LED lamp module in an embodiment as immersion lamp.
Figure 5:
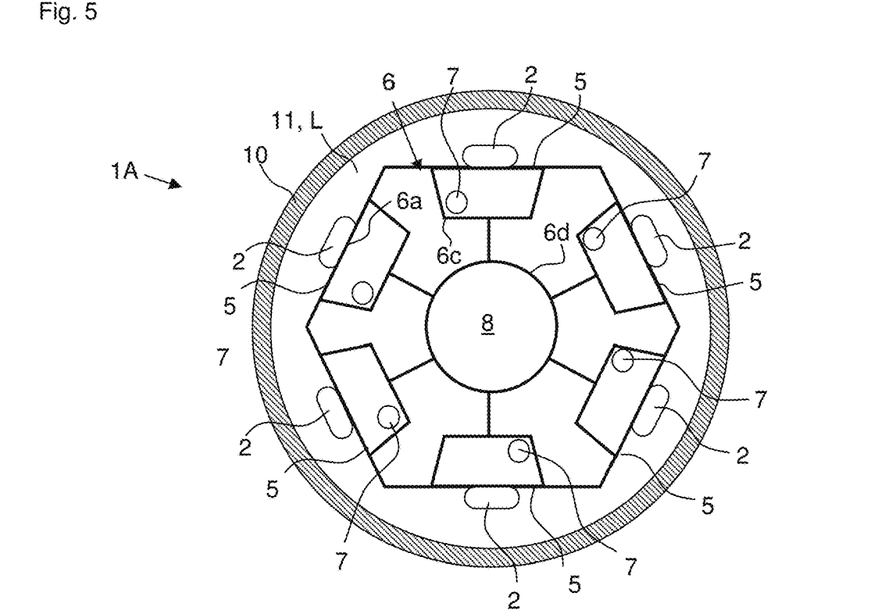
FIG. 5 shows a cross sectional view of the LED lamp module from FIG. 4 along cutting line XX.
Figure 6:
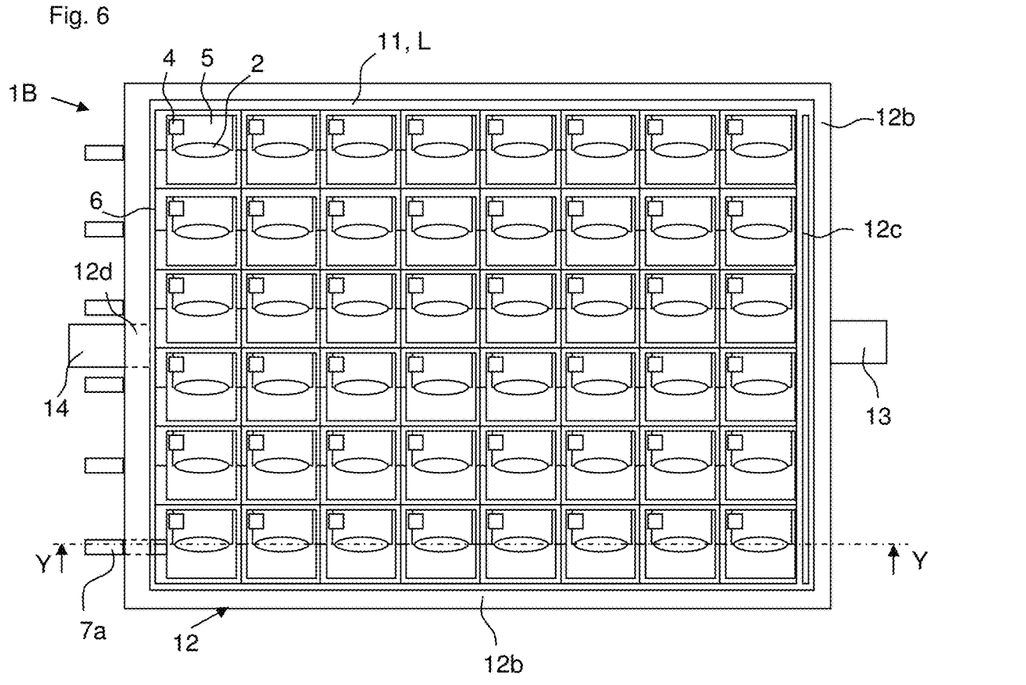
FIG. 6 shows a top view onto an LED lamp module in an embodiment as surface radiator.
Figure 7:
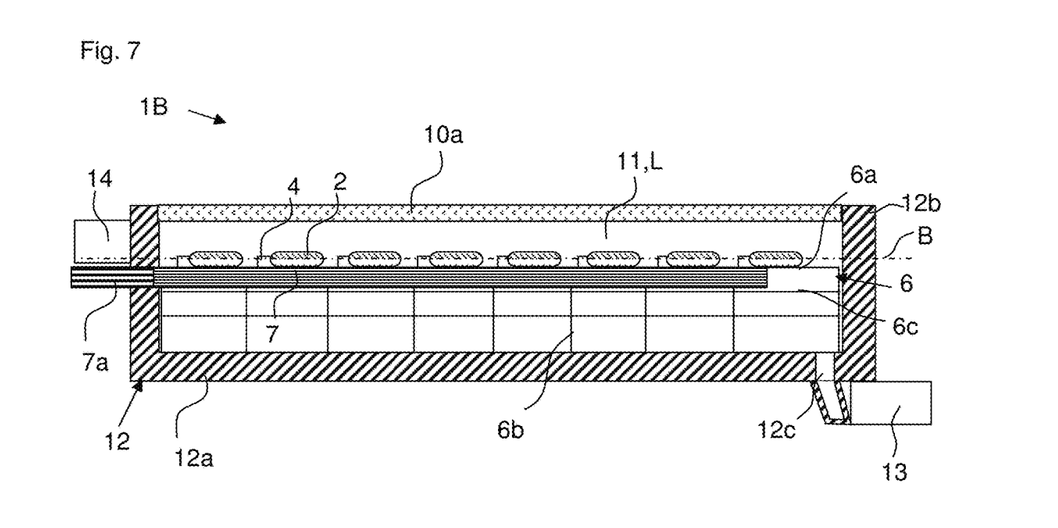
FIG. 7 shows a longitudinal section of the LED lamp module from FIG. 6 along cutting line YY.

FIGS. 4 and 5 show an example for an LED lamp module 1 formed as an immersion lamp 1A, wherein the carrier body 6 has the shape of a geometric prism with the longitudinal axis A. Alternatively, the carrier body of an immersion lamp can also have a cylindrical shape. The LEDs 3 are fastened in LED groups 2 all around to the jacket surface of the prismatic carrier body 6, so that the radiation directions of the LEDs 3 of the LED groups 2 of the immersion lamp 1A run essentially radially to the longitudinal axis A. A further example illustrated in FIGS. 6 and 7 is an LED lamp module 1 formed as surface radiator 1B, in the case of which the carrier body 6 has the shape of a cuboid, which, with a side surface, provides a flat fastening surface for the arrangement of the LEDs 3 in a plane B, so that the radiation direction of the LEDs 3 of the LED surface radiator 1B runs essentially orthogonally to the plane B. In FIGS. 4 to 7, each LED group 2 is illustrated in a simplified manner as ellipsis, an illustration of the individual LEDs 3 as in FIGS. 2 and 3 was forgone therein for the sake of clarity.

It goes without saying that an LED lamp module 1 can also have a shape of the carrier body, which deviates from the two examples, in order to obtain a modified lamp geometry for a different main radiation direction, depending on the intended use. The entire jacket surface of a prismatic or cylindrical carrier body, respectively, further does not need to be used as fastening surfaces for the LEDs, if, for instance, a rotationally symmetrical radiation characteristic is not desired or required for the immersion lamp. A modification of the surface radiator, in contrast, can provide that more than one side surface of the cuboidal carrier body are used as fastening surface in order to, e.g., obtain radiation directions in opposite directions orthogonally to the plane B or radiation directions orthogonally and parallel to the plane B.

Each LED lamp module 1 further has a transparent wall element 10, 10a and a housing element 12, 15, which, together, delimit an interior space 11, in which the carrier body 6 with the LEDs 3 arranged thereon is arranged, so that the transparent wall element 10, 10a is arranged in a corresponding manner to the LEDs 3, in order to allow the radiation emitted by the LEDs 3 to escape. The respective housing element 12, 15 has one or several connecting device(s) 7a for the connection to a (respective) supply line 7 for the electrical connection of the LEDs 3.

In the case of the immersion lamp 1A in FIGS. 4 and 5, the transparent wall element is a cladding tube 10, which is closed on one side and which is arranged coaxially around the carrier body 6 with the LEDs 3. The housing element is a head part 15, which is arranged on the open end of the cladding tube 10. Alternatively to the illustrated example of the cladding tube 10, which is closed on one side, in the case of which the bottom section, which closes the end spaced apart from the head part is formed integrally with the cladding wall, the end spaced apart from the head part of a cladding tube, which is open on both sides, can be closed by means of a stopper.

The surface radiator 1B from FIGS. 6 and 7 has a flat, two-dimensional window pane 10a as transparent wall element, while the housing element is formed as housing 12, which has a base 12a and side walls 12b. The side walls 12b delimit an open surface, which is spaced apart from the base 12a and which is closed by means of the window pane 10a. The carrier body 6 is arranged on the base 12a, so that the fastening surface with the LEDs 3 faces the window pane 10 and the LEDs 3 arranged on the carrier body 6 are arranged between the window pane 10a and the base 12a in a plane B parallel to the window pane 10a. If it is provided in a modification that more than one side surface of the cuboidal carrier body is formed as fastening surface with LEDs, the housing can be modified accordingly, in order to arrange further window panes in a corresponding manner to the fastening surfaces with LEDs. For this purpose, the base and/or the side walls can be formed with corresponding window openings for the arrangement off the further window panes with respect to the LEDs.

For the electrical connection, the LEDs 3 are divided into LED groups 2, which have a predetermined number of LEDs 3 connected in series, as can be seen in FIG. 2. For the sake of clarity, the individual LEDs 3 are not illustrated in FIGS. 4 to 7, but only the LED groups 2. Each LED group 2 is connected to a respective driver device drive 4, which provides a constant current $I_{const}$ for the operation of the LEDs 3 of the respective LED group 2. The driver devices 4, together with the respective assigned LED group 2, are thereby arranged on the carrier body 6 in the interior space 11 of the LED lamp module 1. As can be seen well in FIG. 2, each LED group 2 forms an LED current branch with the assigned driver device 4, which is connected in series, wherein the LED current branches are connected in parallel and are connected to an external constant voltage source $U_{const}$ via the supply line 7.

The number of the connecting devices 7a required on the housing element 15 for a predetermined number of LEDs decreases significantly due to the parallel connection of the LED groups 2, which can be supplied via a single supply line 7 because a connecting device is no longer required per LED strand, as in the prior art. This does not mean, however, that an LED lamp module 1 is limited to an embodiment with a connecting device 7a for an LED circuit with a plurality of parallel LED current branches, which each have a driver device 4 with an LED group 2. On the contrary, an LED lamp module 1, as it is shown by the examples in FIGS. 4 to 7, can have several LED circuits with a plurality of LED current branches connected in parallel, wherein a connecting device 7a is provided on the housing element 12, 15 for the supply line 7 of each LED circuit. Each connecting device thereby has two connecting contacts for a forward and return conductor of the supply line 7. The two connecting contacts can be formed jointly in one connecting plug or in two connecting plugs. Without having to increase the number of the connecting devices 7a, the LED lamp module 1 can be scaled easily, in particular lengthened, by multiplying the LED groups 2, which are connected in parallel, with assigned driver 4, without having to decrease the LED density. Even in the case of longer lamp modules, high LED density or power, respectively, thus can be converted and a largest possible homogeneity of the radiation can thus be attained.

And unlike in the prior art, in which the LEDs are operated at the power maximum, in order to obtain a photon power, which is sufficiently high for the photochemical reactions, the LEDs 3 of the lamp module 1 can be used with high forward current and can be operated in a dimmed manner, in order to ensure a long LED service life.

The LED groups 2, which are connected to a supply line 7 and which are connected in parallel, have a constant number of LEDs 3, for example 15, as in FIGS. 2 and 3. With a forward voltage of 4 V, the supply voltage of the constant voltage source $U_{const}$ then lies at only 60 V DC, so that ATEX plug connectors can advantageously also be used for the connection to the housing element, and the LED lamp module 1 can be used in a region with potentially explosive atmosphere. It is generally quite possible that the LED groups 2 of an LED lamp module 1 also have more than 15 LEDs, so that the supply voltage of the constant voltage source $U_{const}$ at a forward voltage of 4 V lies correspondingly higher, as long as the housing element offers sufficient space for the connection of the supply line(s) 7. The use of ATEX plug connectors, which have larger dimensions for the use with higher voltages, is thus limited and is a function of the dimensioning of the housing element.

In the illustrated examples, each LED group 2 with the assigned driver device 4 is formed as integrated circuit components on a printed circuit board 5, which is fastened to the carrier body 6. In alternative non-illustrated embodiments, however, several LED groups 2 with the assigned driver devices 4 can also be arranged jointly on a printed circuit board 5.

As illustrated schematically in FIG. 3, control and/or regulating elements 9, measuring devices 9a, 9b, 9c, 9d as well as switch elements 9e can also be formed on the printed circuit boards 5 as integrated circuit components, which are assigned to a respective LED group 2. A current measuring device 9a, a voltage measuring device 9b, a temperature measuring device 9c and a photon measuring device 9d can be used as measuring devices 9a, 9b, 9c, 9d, but which do not mandatorily have to be used in combination, as illustrated in FIG. 3. It is also possible to assign only one current measuring device 9a and/or one voltage measuring device 9b to an LED group 2. A temperature measuring device 9c and/or a photon measuring device 9d can also be assigned to several LED groups 2 or can be arranged in the interior space 11 on the carrier body 6 in a group-independent manner.

The control and/or regulating element 9 assigned to an LED group 2 is communicatively connected not only to the respective driver device 4 but also to the or the respective measuring devices 9a, 9b, 9c, 9d and to the switch element 9e, in order to control the switch element 9e and/or the driver device 4 as a function of a measuring value captured by the respective measuring device 9a, 9b, 9c, 9d. By controlling the switch element 9e, the LEDs 3 of the assigned LED group 2 are activated or deactivated as a function of the measuring values. For example, the LED group 2 can be deactivated when the temperature measuring device 9c detects a temperature, which is too high, and/or when the current and/or voltage measuring devices 9a, 9b detect failures of one or several LEDs 3 of the LED group 2. The driver device 4 is controlled for regulating the constant current $I_{const}$, in order to operate the LEDs 3 of the assigned LED group 2 with a predetermined radiation power, for instance when the photon measuring device 9d detects a photon density, which is too low, or when a failure of one or several LEDs 3 detected by means of the current and/or voltage measurement is to be compensated.

Unlike in the example of FIG. 3, in which the control and/or regulating element 9 is formed as integrated circuit component on the printed circuit board 5 of the assigned LED group 2, a control and/or regulating element 9, which is assigned to an LED group 2, can be arranged outside of the interior space 11 in a non-illustrated variation. In both cases, the control and/or regulating elements 9 of the LED groups 2 can be communicatively connected to a higher-ranking control and/or regulating unit 90, as suggested in FIG. 3, in order to adapt the predetermined radiation power of the LEDs 3 of each LED group 2 to one another for homogenous total radiation power. Alternatively, the control and/or regulating elements 9 of the LED groups 2 can be communicatively connected without higher-ranking control and/or regulating unit 90, in order to adapt the predetermined radiation power of the LEDs 3 of each LED group 2 to one another for homogenous total radiation power.

An ID, for instance an identification code, can furthermore be assigned to each LED group 2 by means of the control and/or regulating elements 9 or the higher-ranking control and/or regulating unit 90, in order to identify the printed circuit board 5, e.g., in the case of which a failure of an LED 3 was detected, which is not visible with the naked eye. A deactivation of the affected LED group 2 is thus possible in the case of a fault, whereby it is avoided that the remaining LEDs 3 of the affected LED group 2 are overloaded. Operating data and/or operating time of each LED group 2 can further be collected, in order to simplify the maintenance of the LED lamp module 1.

As can be seen in FIGS. 4 to 7, the carrier body 6 is not embodied in a massive manner, but is formed as carrying cage 6 with a grid structure according to a frame construction, which consists of rod and/or surface elements, which frame openings, which are connected to one another. The carrying cage 6 thereby has carrying structures 6a for fastening the LED groups 2 or the printed circuit boards 5, respectively, and support structures 6b for the positioned arrangement within the interior space 11. The carrying structures 6a of the carrying cage 6 are formed by means of rod and/or surface elements, which lie in the jacket surface of the prism in the case of the LED immersion lamp 1A with the prismatic carrying cage 6 in FIGS. 4 and 5. The support structures 6b, which are likewise formed of rod and/or surface elements, serve for the fastening the carrying cage 6 to the head part 15 on the one hand and for the support on the closed end of the cladding tube 10 on the other hand and thus ensure a centered arrangement within the cladding tube 10.

In the case of the LED surface radiator 1B with the cuboidal carrying cage 6 in FIGS. 6 and 7, the carrying structures 6a and the support structures 6b are likewise formed of rod and/or surface elements, wherein the carrying structures 6a are located on the side surface of the cuboid, which faces the window pane 10a, and the support structures 6b are located on the side surfaces, which face the base 12a and the side walls 12b of the housing 12. The distance of the LEDs 3 from the window pane 10a is determined by means of the dimension of the carrying cage 6 between the carrying structures 6a and the support structures 6b resting on the base 12a.

The carrying cage 6 additionally has a rail structure 6c, likewise of rod and/or surface elements, which form a bus or supply rail 6c, in which the supply line 7 is guided through the interior space 11 to the connecting device 7a on the housing element 12, 15. Shadings of the LEDs 3 are avoided by means of the cable guide provided in this way "behind" the LEDs 3 or the printed circuit boards 5, respectively.

A carrying cage 6 as carrier body 6 for the LEDs 3 is advantageous in particular when the LED lamp module 1 has a cooling circuit K (see FIG. 8, 9) for the circulation of an electrically non-conductive liquid L, which completely fills the interior space 11 and also the openings of the carrying cage 6. For the connection of the interior space 11 to the cooling circuit K, the housing element 12, 15 has an inlet connection 13 and a discharge connection 14, which are illustrated in FIGS. 4 to 7. The electrically non-conductive liquid L thus flows around the LEDs 3 or the printed circuit boards 5, respectively, from both sides in this way, in order to absorb the heat generated by the LEDs 3 and the driver device 4 (and optionally by further circuit components on the printed circuit board 5), which is output by means of the cooling circuit K outside of the LED lamp module 1. In addition to a conveying pump, the cooling circuit K usually has a heat exchanger for this purpose.

In the embodiment as LED immersion lamp 1A illustrated in FIGS. 4 and 5, the head part 15 has passage openings 15a, through which the inlet connection 13 and the discharge connection 14 extend. The inlet connection 13 is thereby connected to a tube structure 6d on the interior space side, which extends longitudinally axially through the carrying cage 6 as coolant inlet section 8. On an end of the interior space 11 spaced apart from the head part, the tube structure 6d thus provides an inlet opening 8a, through which the electrically non-conductive liquid L, which is supplied via the inlet connection 13, flows from the coolant inlet section 8 into the interior space 11. For discharging the electrically non-conductive liquid L from the interior space 11, a discharge opening 14a, which is provided by the eccentrically arranged discharge connection 14, is provided on the end of the interior space 11 close to the head part.

In the case of the LED surface radiator 1B from FIGS. 6 and 7, the housing 12 has, on opposite sides of the interior space 11, an inlet opening 12c connected to the inlet connection 13 and a discharge opening 12d connected to the discharge connection 12. The inlet opening 12c extends through the base 12a directly adjacent to a side wall and widens to a slit parallel to the side wall, which leads into the interior space 11. The discharge opening 12d extends centrally through the opposite side wall. This design of inlet and discharge openings 12c, 12d is to be understood in an exemplary manner, various modifications in shape and number of the openings or by distributor or collector elements between connections and openings are conceivable hereby.

The devices 100 shown in FIGS. 8 and 9 for carrying out a photochemical reaction are to also be understood as examples. Devices 100 can be formed with a different number and/or arrangement of the LED lamp modules 1, which are arranged on or in a photoreactor 101. Unlike illustrated, a device 100 can also have LED lamp modules 1 in a combined manner on or in the photoreactor 101, in order to irradiate the medium presented therein from the outside and inside. The photoreactor 101 can thereby be formed as batch reactor or flow-through reactor. FIG. 8 clarifies the arrangement of LED immersion lamps 1A in the interior of a photoreactor 101, wherein a reaction medium surrounds the immersion lamp 1A. This means that the immersion lamp 1A can be dipped into a reaction medium located in the photoreactor 101, so that the radiation emitted by the immersion lamp 1A reaches directly into the reaction medium. Alternatively, a reactor volume, which contains the reaction medium, can be separated within the photoreactor 101 from the immersion lamp 1A by means of a transparent wall, for instance in order to improve a thermal decoupling or the explosion protection or to guide the reaction medium in a certain flow path along the immersion lamp. For the separation of the immersion lamp 1A for improving the thermal decoupling or the explosion protection, respectively, an additional dip tube (not illustrated) can be used around the cladding tube, wherein the gap lying therebetween can be evacuated or connected to a cooling circuit. For a modified flow path of the reaction medium along the immersion lamp 1A, one or several transparent tubes (not illustrated), can be wound around the immersion lamp, e.g. For the protection or for the temperature control, the interior of the photoreactor 101 can thereby be filled or rinsed with a corresponding gaseous or liquid fluid.

The device 100 outlined in FIG. 9 for carrying out a photochemical reaction provides for the arrangement of LED surface radiators 1B on the side walls of the photoreactor 101, which thus consist of a material, which is transparent for the radiation by the LED surface radiators 1B or which have an opening, in which the LED surface radiator 1B is arranged in a sealed manner with the window pane 10a pointing inwards.

LIST OF REFERENCE NUMERALS

1 LED lamp module
2 LED group
3 LED
4 driver device
5 printed circuit board
6 carrying cage
6a, 6b, 6c, 6d carrying structure, support structure, rail structure, tube structure
7 supply line
7a connecting device
8, 8a coolant inlet section, inlet opening
9 control and/or regulating element
9a, 9b, 9c, 9d current, voltage, temperature, photon measuring device
9e switch element
10 cladding tube
10a disk
11 interior space
12, 12a, 12b housing, base, side wall
12c, 12d inlet opening, discharge opening
13, 14, 14a inlet connection, discharge connection, discharge opening
15, 15a head part, passage opening
100 device for carrying out a photochemical reaction
101 photoreactor
102 control cabinet
L electrically non-conductive cooling liquid
K cooling circuit
$I_{const}$ constant current source
$U_{const}$ constant voltage source

The invention claimed is:

1. An LED lamp module (1), configured for arrangement in a device (100) for carrying out a photochemical reaction, comprising:
a plurality of LEDs (3); and
a carrier body (6) to which the LEDs (3) are fastened,
wherein the carrier body (6) with the LEDs (3) is arranged in an interior space (11) of the LED lamp module (1),
wherein the interior space (11) is delimited by a transparent wall (10, 10a) and by a housing (12, 15),
wherein the transparent wall (10, 10a) is arranged in a corresponding manner to the LEDs (3),
wherein at least one electrical supply line (7) for electrically connecting the LEDs (3) extends through the housing (12, 15),
wherein the plurality of LEDs (3) is divided into LED groups (2),
wherein each of the LED groups (2) has a predetermined number of LEDs (3),
wherein the LEDs (3) of each LED group (2) are connected in series, and
wherein each LED group (2) is connected to a respective driver device (4) as a constant current source ($I_{const}$) for operating the LEDs (3) of the respective LED group (2),
wherein each driver device (4) is arranged on the carrier body (6) in the interior space (11) of the LED lamp module (1) adjacent to the LED group (2) to which is connected,
wherein each driver device (4) is connected in series to the respective LED group (2) and forms an LED current branch, and
wherein the LED current branches are connected in parallel to a constant voltage source ($U_{const}$) via the electrical supply line (7).

2. The LED lamp module (1) according to claim 1,
wherein the predetermined number of LEDs (3) of all LED groups (2) is identical and at most 25.

3. The LED lamp module (1) according to claim 1,
wherein the LED current branches from the LED groups (2) with the driver devices (4) connected to them are formed as integrated circuit components on printed circuit boards (5),
wherein the printed circuit boards (5) are fastened to the carrier body (6), and wherein one or several of the LED groups (2) with the driver device (4) connected to them is/are arranged on each printed circuit board (5).

4. The LED lamp module (1) according to claim 3, wherein each LED group (2) is connected to
at least one control and/or regulating element (9), and
at least one measuring device (9a, 9b, 9c, 9d) selected from a group consisting of a current measuring device (9a), a voltage measuring device (9b), a temperature measuring device (9c), and a photon measuring device (9d), and
at least one switch (9e), and
wherein the control and/or regulating element (9) is communicatively connected to the at least one measuring device (9a, 9b, 9c, 9d) and is configured
to control the switch (9e) as a function of a measuring value captured by the at least one measuring device (9a, 9b, 9c, 9d), in order to activate or deactivate and/or to dim the LEDs (3) of the connected LED group (2) and/or
to control the driver device (4) of the connected LED group (2) as a function of the measuring value captured by the at least one measuring device (9a, 9b, 9c, 9d) for regulating the constant current ($I_{const}$), in order to operate the LEDs (3) of the connected LED group (2) with a predetermined power.

5. The LED lamp module (1) according to claim 4, wherein the measuring device (9a, 9b, 9c, 9d) and/or the switch (9e) are arranged on the printed circuit board (5) of the connected LED group (2) as integrated circuit components.

6. The LED lamp module (1) according to claim 4, wherein the control and/or regulating element (9) is arranged on the printed circuit board (5) of the connected LED group (2) or outside of the interior space (11) as an integrated circuit component,
wherein the control and/or regulating elements (9) are communicatively connected to one another and/or to a higher-ranking control and/or regulating unit (90) and are configured
to adapt a predetermined radiation power of the LEDs (3) of each LED group (2) to one another and/or
to assign an ID to each LED group (2) and/or
to collect operating data and/or operating time of each LED group (2).

7. The LED lamp module (1) according to claim 1, wherein the LED lamp module (1) has at least one supply rail (6c) for receiving the at least one line (7) within the interior space (11).

8. The LED lamp module (1) according to claim 7, wherein the carrier body (6) is a carrying cage (6) with a grid structure,
wherein the carrying cage (6) comprises carrying structures (6a),
wherein the LED groups (2) are fastened to the carrying structures (6a), and
wherein the carrying cage (6) has at least one support structure (6b) for positioned arrangement within the interior space (11).

9. The LED lamp module (1) according to claim 8, wherein the at least one supply rail (6c) is provided by at least one rail structure (6c) of the carrying cage (6).

10. The LED lamp module (1) according to claim 8, wherein the LED lamp module (1) has a cooling circuit (K) with an electrically non-conductive liquid (L), wherein the housing (12, 15) has an inlet connection (13) and a discharge connection (14) for the connection of the interior space (11) to the cooling circuit (K), so that the interior space (11) is completely filled with the electrically non-conductive liquid (L).

11. The LED lamp module (1) according to claim 10, wherein the LED lamp module (1) is formed as an immersion lamp (1A) with a longitudinal axis (A),
wherein the transparent wall (10, 10a) is a transparent cladding tube (10),
wherein the transparent cladding tube (10) is closed on one side and arranged coaxially around the carrier body (6) with the LEDs (3),
wherein the housing (12, 15) has a head part (15), and
wherein the head part (15) is arranged on an open end of the cladding tube (10).

12. The LED lamp module (1) according to claim 11, wherein the carrier body (6) is formed as a carrying cage (6),
wherein the carrier body (6) has, on at least one longitudinally axial end, the at least one support structure (6b) for the positioned arrangement within the interior space (11),
wherein the support structure (6b) is formed for centered arrangement on the head part (15) and/or the closed end of the cladding tube (10), and/or
wherein the head part (15) has passage openings (15a),
wherein the inlet connection (13) and the discharge connection (14) each extend through one of the passage openings (15a) or are connected thereto, and
wherein on the side of the interior space the inlet connection (13) is connected to a tube structure (6d),
wherein the tube structure (6d) is arranged in the carrier body (6) formed as a carrying cage (6) and extends longitudinally through the carrying cage (6) as a coolant inlet section (8),
wherein the coolant inlet section (8) provides an inlet opening (8a) on an end of the interior space (11) spaced apart from the head part,
wherein the discharge connection (14) extends through the head part (15) or the passage opening (15a) connected to the discharge connection (14) provides a discharge opening (14a) on an end of the interior space (11) close to the head part.

13. The LED lamp module (1) according to claim 12, wherein the LED lamp module (1) is formed as a surface radiator (1B),
wherein the transparent wall (10, 10a) is a transparent flat window pane (10a),
wherein the housing (12) has a base (12a) and side walls (12b),
wherein the window pane (10a) closes an open surface,
wherein the open surface is delimited by side walls (12b), and
wherein the LEDs (3) arranged on the carrier body (6) are arranged between the window pane (10a) and the base (12a) in a plane (B) parallel to the window pane (10a).

14. The LED lamp module (1) according to claim 13, wherein the carrier body (6) is arranged with the at least one support structure (6b) on the base (12a) of the housing (12), and
wherein the carrying structures (6a), to which the LEDs (3) are fastened, are formed on a side of the carrying cage (6) facing away from the at least one support structure (6b),
wherein a dimension of the carrying cage (6) between the carrying structures (6a) and the at least one support structure (6b) determines a distance of the LEDs (3) from the window pane (10a), and/or
wherein the housing (12) has, on opposite sides of the interior space (11), at least one inlet opening (12*c*), which is connected to the inlet connection (13), and at least one discharge opening (12*d*), which is connected to the discharge connection (12).

15. A device (100) for carrying out a photochemical reaction,
wherein the device (100) has a photoreactor (101), on or in which at least one lamp module is arranged,
wherein the at least one lamp module emits radiation with a wavelength,
wherein the wavelength is suitable for the photochemical reaction,
wherein the lamp module is an LED lamp module (1) according to claim 1.

* * * * *